United States Patent [19]

Ashida et al.

[11] Patent Number: 4,626,385

[45] Date of Patent: Dec. 2, 1986

[54] N-SUBSTITUTED CARBAMOYL-LACTAM

[76] Inventors: Kaneyoshi Ashida, 23560 E. Newell Cir., Farmington Hills, Mich. 48024; Jozef L. M. van der Loos, Rijksweg Zuid 146, 6134 AE Sittard, Netherlands

[21] Appl. No.: 736,257

[22] Filed: May 21, 1985

Related U.S. Application Data

[63] Continuation-in-part of Ser. No. 592,082, Mar. 22, 1984, abandoned.

[51] Int. Cl.$^4$ ................. C07D 223/10; C07D 207/38; C07D 211/40
[52] U.S. Cl. ................................ 540/451; 546/243; 548/550; 528/315; 540/525
[58] Field of Search ................. 260/239.3 R; 546/243; 548/530

[56] References Cited

U.S. PATENT DOCUMENTS 3,245,961 4/1966 Fetscher et al. .................... 260/77.5
3,511,893 5/1969 Scharffer et al. .................. 260/85 S
4,502,821 7/1983 Hodek et al. ........................ 502/153

FOREIGN PATENT DOCUMENTS 1067153 5/1967 United Kingdom .............. 260/77.5
1099265 1/1968 United Kingdom .............. 260/77.5

OTHER PUBLICATIONS

Hedercik et al, "A New RIM System from Nylon 6 Block Co-polymers: Chemistry and Structure", AIChe Nat. Summer Meeting, Det., Mich., (8/81).

Allen et al., "Caprolactam Based Block Copolymers Using Polymeric Activators", Die Angewandte Makromolekulare Chemie, vol. 58/59, No. 844, pp. 321-343, (1977).

Primary Examiner—Robert T. Bond
Attorney, Agent, or Firm—Cushman, Darby & Cushman

[57] ABSTRACT

An N-substituted carbamoyl-lactam compound of the formula

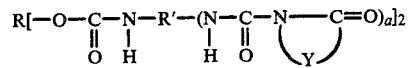

wherein
R is a di-valent radical derived from polytetramethylene glycol, R' is an at least divalent radical derived from a diisocyanate, Y is a $C_3$-$C_{14}$ ring-forming alkylene group, and a has a value of at least 1 and is a number corresponding to the mean functionality of the aforesaid polyisocyanate minus 1. A process for preparing the N-substituted carbamoyl-lactam compound is also described.

9 Claims, No Drawings

N-SUBSTITUTED CARBAMOYL-LACTAM

RELATED APPLICATIONS

This application is a continuation in part of U.S. application Ser. No. 592,082 filed on Mar. 22, 1984 now abandoned, is hereby incorporated by reference.

FIELD OF THE INVENTION

The present invention relates to a N-substituted carbamoyl-lactam and a novel process for preparing a lactam compound.

BACKGROUND OF THE INVENTION

In the anionic polymerization of lactam, especially E-caprolactam, an anionic polymerization catalyst and an activator (or promoter) are typically present. Various kinds of activators are disclosed in the art.

One proposal for an activated anionic catalytic polymerization process is described in U.S. Pat. No. 3,304,291. The activator used therein consists of organic nitrogen compounds having on at least 2 to 12 carbon hydrocarbon radical being an N-substituted compound of at least one urea, thiourea or guanidine radical.

An improvement thereon for producing polylactams having a higher notch impact strength includes conducting the activated anionic catalyzed lactam polymerization process in the presence of a quantity of a polyether soluble in the molten lactam or the mixture of lactams being polymerized. the polyether is limited to at most about 25% by weight of the quantity of the lactam to be polymerized, otherwise the resultant polylactams possess poor mechanical properties.

An isocyanate promoter having at least one isocyanate compound has been used in an anionic catalytic polymerization of a lactam conducted in the presence of a polyether soluble in molten lactam.

As further described in U.S. Pat. No. 3,704,280, it is required that the absolute number of hydroxyl (OH) groups contained in the polyether is greater than the absolute number of isocyanate groups contained in the isocyanate employed.

Another improved process for the anionic catalytic polaymerization of lactams aided by one or more promoters described in U.S. Pat. No. 3,770,689 includes adding to the reaction mixture one or more polyether compounds having etherified hydroxyl groups which are soluble in the molten lactam or lactam mixture. Conventional promoters suitable for use therein include polymer chains permanently terminated on at least one end by a promoter function. Generally the promoter functional groups or substituents are similar to monomeric promoters such as acid-chloride groups, isocyanates, N-carbonyl-lactam groups, imide groups, N-carbonyl-sulfonamide groups, N-carbonyl-urea groups and acid-anhydride groups.

U.S. Pat. No. 3,987,033 describes a composition prepared by reacting an aromatic diisocyanate with a tripimary alcohol and subsequently reacting this product with a mixture of a hydroxy component such as a phenol.

U.S. Pat. No. 4,171,305 describes pure crystals of E-caprolactam diblocked w,w'-diisocyanato-1,3-dimethylbenzene used as a hardener of powder coating composition.

U.S. Pat. No. 4,211,699 describes isocyanate adduct diols derived from an amino diol or a hydrazine diol and an organic diisocyanate and their use for the production of self-crosslinkable and/or self-crosslinked polyurethanes.

U.S. Pat. No. 3,018,273 describes a process for in situ polymerizing caprolactam in the presence of an organomagnesium initiator compound, and an N,N diacyl promoter compound. Preferably, the N, N diacyl promoter compounds are N-substituted imides, such as cyclic imides of dicarboxylic acids, having molecular weights not exceeding 1000 in order to preclude the presence of large inert groups in the promoters. The molecular weights preferably do not exceed 500.

British Pat. No. 1,067,153 describes a process for preparing nylon-block-copolymers by anionically polymerizing caprolactam in the presence of an isocyanate capped polypropylene glycol and a potassium based catalyst. In this process a nylon block copolymer containing at least one polyether block is formed.

In the U.S. Pat. Nos. 3,862,262, 4,031,164, 4,034,015 and 4,223,112 various aspects of the preparation of nylon block copolymers from caprolactam in the presence of an acyl lactam activator are described. U.S. Pat. No. 3,862,262 describes lactam-polyol-acyl-polylactam block-terpolymers. U.S. Pat. Nos. 4,031,164 and 4,223,112 describe lactam-polyol-polyacyl-lactam-block terpolymers having a specified ratio of the various components. More particularly U.S. Pat. No. 4,031,164 discloses the use of 18 to 90% by weight of polyol blocks in the terploymer. U.S. Pat. No. 4,034,015 is directed to lactam polyol-polyacyllactam or lactam-polyol-acyl-poly-lactam block terpolymers having at least about 5% ester end group termination.

Reissue Pat. No. Re. 30,371 describes the preparation of polyester-polyamide compounds by condensation of an alcohol and an acyl lactam in the presence of at least one of a metal or metal compound, the metal components thereof being selected from Group IA, IIA, IIB and IIIa of the Periodic Table.

Preparation of nylon compositions by anionicaly polymerizing at least 75% lactam with up to about 25% of an epoxy component in the presence of a basic catalyst and promoter is disclosed in U.S. Pat. No. 4,400,490. The promoters are those typically used in the anhydrous polymerization of lactams.

It has been suggested in a paper by Sibal et al, Designing Nylong Polymerization Systems, apparently presented in part at the 2nd International Conference on Reactive Polymer Processing, Pittsburge, Pa. in November 1982. Connection with the anhydrous anionic polymerization of caprolactam to prepare a co-catalyst or initiator by reacting isocyanate with dried caprolactam at 80° C. Initially, the dried caprolactam may be heated and about 20% thereof boiled off with the residue portion being reacted with an isocyanate, the isocyanate being obtained by slowly reacting 1 mole polypropylene glycol (M.W. 2000) with 2 moles hexamethylene diisocyanate. However, it is clear that further work is needed to determine processability of polylactams produced using this promoter.

The published (Dec. 22, 1983) European patent Applications Nos. 67693 and 67694 describe specific lactam compounds based on various kinds of hydroxy compounds. The published (Dec. 22, 1983) European Patent Applications Nos. 67694 and 67695 describe the use of these lactam compounds in the preparation of nylon.

Serious defects of prior experimental nylon block copolymers included relatively high water absorption.

That results in lowered mechanical strengths of "RIM" nylon products.

Additional disadvantages associated with prior experimental nylon block copolymers have included relatively long mold retention times, inferior surface appearances, and decreased polymer strengths caused by incorporation of various copolymer blocks. These disadvantages are most manifest in comparison to reaction-injection molded urethanes.

SUMMARY AND OBJECTS OF THE INVENTION

The present invention relates to certain novel N-substituted carbamoyl lactam compounds and a process for preparing such novel compounds. The novel N-substituted carbamoyl lactam compounds are prepared from polytetramethlyene glycol, a polyisocyanate and a lactam.

The present invention provides an N-substituted carbamoyl-lactam compound which can be used as an activator in the preparation of nylon block copolymers, having improved physical properties.

More advantageously, nylon block copolymers prepared from the present novel n-substituted carbamoyl lactam activators have significantly reduced water absorption properties.

DESCRIPTION OF THE INVENTION

The present invention relates to certain N-substituted carbamoyl lactam compounds and to a process for preparing the certain N-substituted carbamoyl lactam compounds.

The Novel N-Substituted Carbamoyl Lactam Compounds

The novel compounds of the present invention are characterized by the formula

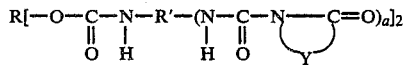

wherein

R is a di-valent hydrocarbon residue radical derived from polytetramethylene ether glycol, and represents the radical remaining from the polytetramethylene oxide material used in preparing the polytetramethylene glycol, R' is a multivalent hydrocarbon radical derived from a polyisocyanate.

Y is a $C_3$-$C_{14}$ ring forming alkylene group, and a has a value of at least 1.

Surprisingly, it has been found that nylon block copolymers prepared from these N-substituted carbamoyl-lactam compounds have superior properties compared with the nylon block copolymers prepared from N-substituted carbamoyl lactam compounds based on other diols such as poly(oxyethylene)glycol or poly(oxypropylene) glycol.

Surprisingly and most advantageously, nylon block copolymers prepared using these novel n-substituted carbamoyl lactam activators exhibit excellent, i.e. low, water absorption properties.

The novel compound of the present invention can be used as activators in combination with a lactam polymerization catalyst, in the preparation of nylon block copolymers.

The di-valent hydrocarbon residue, R, is derived from polytetramethylene ether glycol (PTMG). The equivalent weight of the polytetramethylene ether glycol is advantageously at least 300. More advantageously the equivalent weight is about 1000 to 3000, and still more advantageous is an equivalent weight of about 1000 to 2500. An exemplary suitable polytetramethylene glycol is manufactured by Quaker Oats Co. under the tradename Polymeg 1000 and by Du Pont under the tradename Teracal. It is also possible that the divalent hydrocarbon residue may be derived from polytetramethylene ether glycol and one or more other polyoxyalkylene ether polyols of diols, triols or tetraols. These polyols can be of the same molecular weight as indicated above. It is, however, possible to use one or more low molecular weight polyols such as glycerol or trimethylol-propane.

It is to be understood that any molecular weights, or equivalent weights, referred to herein are numerical average weights. Furthermore, the term equivalent weight of a polyol is understood to mean the numerical average weight of the polyol per hydroxyl group, i.e. the molecular weight divided by the functionality.

Various polyisocyanates are suitable for use in the present process. Broadly speaking, such polyisocyanates having an isocyanate functionality of two or more include aliphatic, araliphatic, cycloaliphatic and aromatic isocyanates. Examples include hexamethylene diisocyanate (HDI), isophorone diisocyanate (IPDI), and xylylene diisocyanate (XDI). Readily available suitable diisocyanate and polyisocyanates include 2,4-toluene diisocyanate, 2,6-toluene diisocyanate, and 2,2'-, 2,4'-, and 4,4'-diphenylmethane diisocyanate (MDI or crude MDI). Other suitable exemplary polyisocyanates include polyphenylene polymethylene polyisocyanates, modified MDI (e.g. carbodiimide modified MDI), and the hydrogenated aromatic diisocyanates such as hydrogenated TDI, XDI or MDI. A suitable hydrogenated xylylene diisocyanate is available from Takeda Chemical Ind. Co. under the name Takenate 600. A suitable HDI product is Mondur HX from Mobay Chemical Co. Also suitable are the three or higher functional polyisocyanates, including the isocyanurate containing trimers of two or more diisocyanates. These isocyanates may be employed singly or in mixed form.

The value of a as given in the formula described herein-before, depends on the functionality of the isocyanate used. The value of "a" is the mean functionality of the polyisocyanate (f) minus one (a=f−1). Thus, if a substantially pure diisocyanate is used, the value of "a" is 1. If, on the other hand, a tri or higher functional polyisocyanate is used, such as an isocyanurate containing trimer, the value of "a" will be two or higher.

Process for Preparing the Novel N-Substituted Carbamoyl Lactam

The present invention is also directed to a process for preparing the N-substituted carbamoyllactam compounds as described hereinabove. The process includes admixing polytetramethylene ether glycol with a polyisocyanate to produce an isocyanate terminated polyurethane prepolymer. Optionally, if desired, the polytetramethylene ether glycol and polyisocyante are mixed in the presence of a polyurethane catalyst. The polyurethane prepolymer is subsequently reacted with a lactam.

The polytetramethylene ether glycol has an equivalent weight of at least 300. More advantageously, the equivalent weight is that 1000 to 3000, and more advantageously still the molecular weight is from 1000 to 2500. An admixture of polytetramethylene ether glycol with another polyol can be employed as long as at least 50% of all the hydroxyl groups available for reacting with the polyiso-cyanate will originate from the polytetramethylene ether glycol. More advantageously, if the mixture of polytetramethylene glycol and another polyol is used in preparing the N-substituted-carbamoyl lactam compound, then the OH equivalent originating from the polytetramethylene glycol is about 60% to 95%. The above-mixture may thus contain, in addition to the polytetramethylene ether glycol one or more other polyoxyalkylene polyols of diols, triols, or tetraols. The other polyoxyalkylene polyols have molecular weights within the above-ranges; however, low molecular weight polyols such as glycerol or trimethylol propane can be used.

Various lactams are suitable for use in preparing the novel N-substituted carbamoyl lactams. Generally, lactams having from 4 to about 14 carbon atom rings are suitable and lactams having from 5 to 11 carbon atoms are preferred. The number of carbon atoms in the lactam ring will, of course, related to the number of carbon atoms in the "Y" group in the N-substituted carbamoyl-lactam. Lactams may have straight chain or branched chain alkyl substituents on the lactam ring. The alkyl substitutents do not inhibit or adversely affect preparation of the activator or the subsequent use thereof. Exemplary lactams include, for example, 2-pyrrolidone, 2-piperidone, lauryl lactam, caprolactam and the like. Alkyl substituted lactams include, for instance, 6-amino-5-methyl hexanoic acid lactam and 6-amino-3-methyl-hexanoic acid lactam. Advantageously, caprolactam is used.

The N-substituted carbamoyl lactam compounds are advantageously used as activators in the preparation of nylon-block copolymers (anionic polymerization), by admixing a lactam, such as caprolactam, a lactam polymerization catalyst and the activator of the invention. Advantageously, the amount of catalyst used can range from 0.01 wt. % to 10 wt. %, with respect to the lactam. More advantageously the amount of catalyst used can advantageously range between 0.10 wt. % and 2 wt. %. The amount of activator with respect to the final product lies advantageously between 5 wt. % and 35 wt. %. Preferably the amount advantageously ranges between 10 wt. % and 25 wt. % Within the ranges the combination of impact strength and flexural modulus of the nylon block copolymer is optimal. The amount of polyether (the rubbery component in the nylon block copolymer) with respect to the final nylaon block copolymer can be varied, for instance, by using different lactam to adduct ratios.

Generally, increasing the amount of catalyst increases the rate of copolymerization.

Increasing the quantity of the prepolymer adduct increases the copolymerization rate. For example, at a constant amount of a catalyst (weight %) at 140° C. a 75/25 capralactam to adduct mix solidified in about 15 minutes whereas a 25/75 caprolactam to adduct solidified in only about 7 minutes.

Suitable lactam polymerization catalysts include sodium lactamate, potassium lactamate or bromomagnesium lactamate. Advantageously, the polymerization of a lactam and the activator of the present invention is conducted in the presence of potassium lactamate. Surprisingly, the polymerization reaction catalyzed with the potassium lactamate catalyst proceeds at a more rapid rate and at a lower temperature than a polymerization catalyzed with Grignard lactamate catalysts.

The anionic polymerization of lactams is advantageously conducted at a temperature between the melting point of the lactam and the melting point of the resulting nylon block copolymer. Preferably, the polymerization is conducted at a temperature between 90° C. and 160° C.

Various testing methods are used in evaluating the nylon block copolymers. The tests followed accepted standard methods. The flexural modulus was determined according to ASTM D-790. Tensile and elongation strengths were measured according to ASTM method D-421. The crosshead speed employed was 5 inches/min. A microdie was used to cut the specimens. The Shore-D hardness of the product was determined according to the ASTM method D-2240. The tear resistance of product samples was measured by the ASTM method D-624. Thermal Stability: The thermal stability of the samples was measured by TGA (Thermogravimetric analysis). The ASTM method E-537-76 was used. The TGA analyzer employed was the DuPont Model 950. Izod impact strength of product samples was determined according to the ASTM D-256 method. The water absorption study of the product samples was conducted by using approximate sizes of 2.2×1.3×0.4 cm dipped into distilled water at room temperature (23° C.) for 24 hours, thereafter the readings were noted and the reading after one week was also noted. The change in weight of the sample was considered as the percent of water absorbed.

Unless stated otherwise herein, CLM and caprolactam designate E-caprolactam. Also nyrim catalyst means a bromomagnesium lactamate.

EXAMPLES

Example 1

300 grams (0.60 equivalent) of a polytetramethylene ether glycol having a molecular weight of 1000 (Polymeg 1000 from (Quaker Oats Co.) and hexamethylene diisocyanate in an amount of 104 grams (1.24 equivalent) were were admixed and charged in a reaction kettle, and heated at 80° C. for one hour and 45 min. to obtain an isocyanate-terminated prepolymer having a NCO percent of 6.65. 72.9 grams (0.64 mole) of caprolactam was added to the isocyanate-terminated prepolymer and heating was continued thereafter for 2 hours at 85° C.

The resultant adduct was highly viscous at room temperature, and was liquid at 65° C.

The adduct was copolymerized with caprolactam in the presence of Nyrim Catalyst Concentrate (a Grignard lactamate produced by Monsanto Company).

Table I reports the results of a rate study. The reported rate study shows that the rate of copolymerization in terms of elapsed solidification time decreases in accordance with the increasing amount catalyst and an increasing amount of adduct in the copolymer.

TABLE I

| Rate Study of HDI Adduct at 140° C. | | | |
|---|---|---|---|
| Product No. activator | Catalyst eq. % | Polyether wt. % | Solidification Time |
| 1 | 4.1 | 11.3 | 15 min. |
| 2 | 5.0 | 22.6 | 12 min. |
| 3 | 6.9 | 33.9 | 7 min. |

Example 2

300 grams (0.60 equivalent) of a polytetramethylene ether glycol (Polymeg 1000 from Quaker Oats Co.) and hexamethylene diisocyanate in an amount of 104 grams (1.24 equivalent) were admixed and charged into a reaction kettle, and heated at 80° C. for one hour and 45 min. to obtain an isocyanate-terminated prepolymer having a NCO percent of 6.65. 72.9 grams (0.64 mole) of caprolactam was then added to the isocyanate-terminated prepolymer in the reaction kettle. Heated was continued thereafter for 2 hours at 85° C.

The resultant adduct was highly viscous at room temperature, and was liquid at 65° C.

The adduct was copolymerized with caprolactam in the presence of a potassium lactamate catalyst. The procedure followed was the same as in Example 1 except for the substitution of potassium lactamate for the Nyrim Catalyst Concentrate.

The potassium lactamate catalyst yielded a much faster rate solidification at even lower temperatures than the Nyrim Catalyst Concentrate (a Grignard lactamate) used in Example 1. In this example, the copolymerization was conducted at 130° C. whereas the copolymerization of Example 1 was conducted at 140° C. The results of a rate study are reported below in Table II. In the Table II, HDI stands for 1,6 hexane diisocyanate.

TABLE II

Rate Study of HDI Adduct at 130° C.
Using a Potassium Lactamate Catalyst

| Product No. | Catalyst eq. % | Polyether wt. % | Solidification Time |
|---|---|---|---|
| 13 | 2.1 | 10.2 | 2 min. 30 sec. |
| 14 | 3.1 | 10.2 | 1 min. 55 sec. |
| 15 | 6.3 | 10.2 | 2 min. 20 sec. |
| 16 | 3.3 | 20.2 | 2 min. 40 sec. |
| 17 | 6.5 | 20.2 | 1 min. 55 sec. |

Example 3

120 grams (1.24 equivalent) of hydrogenated xylylene diisocyanate (Takenate 600 from Takeda Chemical Ind. Co.) and 300 grams (0.60 equivalent) of polytetramethylene ether glycol (Polymeg 1000 from Quaker Oats) were admixed and charged into a reaction kettle. The mixture reacted at for 2.2 hours at 75° C. 72.3 grams of caprolactam was added to the reaction kettle. The reaction kettle was heated for 2 hours at 85° C.

Table III shows the rate of copolymerization with ξ-caprolactam using one catalyst. Product Nos. 4, 5 and 6 show the rate of copolymerization using bromomagneisum lactamate. The amount of Caprolactam was varied and therefore the weight percent of the polyether in the nylon 6 block copolymer product varied from 32.8 wt. % to 10.9 wt. %. The equivalents and weight percents relate to component ratios of the reactants used in preparing the products.

TABLE III

Rate Study of H₆XDI-Polymeg 100 adduct at 140° C.

| Product No. activator | Polyether wt. % | Catalyst eq. % | Solidification Time |
|---|---|---|---|
| 4 | 32.8 | 6.5 | 11 min. |
| 5 | 21.9 | 5.0 | 16 min. |
| 6 | 10.9 | 4.1 | 20 min. |

Example 4

120 grams (1.24 equivalents) of hydrogenated xylylene diisocyanate, (Takenate 600 from Takeda Chemical Ind. Co.) and 300 grams (0.60 equivalent) of polytetramethylene ether glycol (Polymeg 100 from Quaker Oats) were admixed and charged into a reaction kettle. The mixture reacted for 2.2 hours at 75° C. 72.3 grams of caprolactam was added to the thus obtained intermediate reaction product and heating continued thereafter for 2 hours at 85° C.

The above intermediate reaction product, i.e. adduct, was copolymerized with E-caprolactam. In these copolymerizations reaction mixtures, i.e. streams were used. Stream A contained the catalyst and E-caprolactam. Stream B contained the adduct and E-caprolactam. The products were prepared by admixing stream A and stream B and injecting the mixture into the mold. The admixture was prepared at 95° and the copolymerization was conducted at 130° C.

The rate of copolymerization was investigated by substituting a potassium lactamate catalyst for the bromomagnesium lactamate of Example 3. It was now possible to conduct the polymerization at a lower temperature, 130° C. The study shows rapid reactions were obtained at reduced catalyst equivalent percent s compared to Example 3. The results of the rate study are shown in Table IV.

TABLE IV

Rate Study of H₆XDI-Polymeg 100 adduct at 130° C.

| Product No. | Polyether wt. % | Catalyst eq. % | Solidification Time |
|---|---|---|---|
| 19 | 20.1 | 2.2 | 2 min. 50 sec. |
| 20 | 20.1 | 3.2 | 1 min. 55 sec. |
| 21 | 20.1 | 6.5 | 1 min. 30 sec. |

Example 5

177 grams of Isonate 143L (a liquified MDI, isocyanate equivalent of 144, from Upjohn) was charged in a reaction kettle.

300 grams of Polymeg 1000 was mixed with 50 grams of dioxane, and then the thus obtained solution of Polymeg 1000 in dioxane was added drop-by-drop into the Isonate 143L in the reaction kettle. The reaction temperature was elevated slowly up to 80° C. The reaction time was noted as one hour and 35 minutes to reach the theoretical NCO % (5.45%). A prepolymer was thus formed.

A stoichiometric amount of ξ-caprolactam (71.3 grams) was then charged into the reaction kettle. The prepolymer and the caprolactam reacted to provide a caprolactam-terminated adduct.

The dioxane solvent was removed under vacuum after the adduct was prepared.

Copolymerizations of the adduct with E-caprolactam using a bromo magnesium lactamate catalyst are shown in Table V.

TABLE V

Reaction Rate of MDI Adduct (1:2)
and MDI Adduct (1:3) Mole at 140° C.

| Product No. | Activator eq. % | Polyether (wt. %) | Catalyst (eq. %) | Cloud Point | Solidification Time 1:2 Mole | Solidification Time 1:3 Mole |
|---|---|---|---|---|---|---|
| 7 | 13.7 | 29.3 | 6.6 | * | 18 min. | 70 min. |
| 8 | 7.0 | 19.6 | 5.1 | * | 19 min. | 35 min. |

TABLE V-continued

Reaction Rate of MDI Adduct (1:2) and MDI Adduct (1:3) Mole at 140° C.

| Product No. | Activator eq. % | Polyether (wt. %) | Catalyst (eq. %) | Cloud Point | Solidification Time 1:2 Mole | 1:3 Mole |
|---|---|---|---|---|---|---|
| 9 | 2.8 | 9.8 | 4.1 | 16 min. | 24 min. | 10 min. |

*After Solidification Time

Example 6

A TDI-terminated prepolymer was prepared. Toluene diisocyanate and Polymeg 1000 (polytetramethylene ether glycol having a molecular weight of 1000) were admixed at a 2:1 molar ratio in the presence of 0.1% of T-9 (Tin) catalyst. The reaction mixture was heated at 80° C. for 1.5 hours to reach nearly theoretical NCO percent in the thus obtained prepolymer.

Then, a stoichiometric amount of caprolactam was added to the TDI-terminated prepolymer, and the mixture was reacted at 80° C. for 2 hours. The reaction mixture was almost solid at room temperature.

The caprolactam adduct of the TDI-terminated urethane prepolymer did not completely copolymerize with caprolactam, and the reaction product after one hour was a highly viscous liquid, and was not solid.

Example 7

(a) Preparation of an MDI adduct.

A MDI-terminated urethane prepolymer was prepared by using Polymeg 1000 and Isonate 143L (a liquified MDI). The MDI and Polymeg 1000 were admixed at different molar ratios.

At a 2:1 molar ratio of Polymeg 1000 to Isonate 143L, the resulting prepolymer was highly viscous and was very difficult to handle.

Therefore, the molar ratio was changed to 3:1. Accordingly, the reaction product also contained a MDI-caprolactam adduct of low molecular weight. The preparation procedures employed were almost the same as those employed in Example 6 with the TDI prepolymer.

The thus obtained adduct was solid at room temperature and melted at about 90° C.

(b) Copolymerization of MDI Adduct.

The adduct composed of MDI-terminated Polymeg 1000-based urethane prepolymer (25 parts by weight), caprolactam (75 parts by weight) and a 1 molar solution of bromo magnesium lactamate in caprolactam (40 parts by weight) were mixed in a beaker at 145° C. for 10 min., and its viscosity was increased to sufficient level. The reactants were then transferred to a mold maintained at 145° C. After one minute and 30 seconds, the reacting mass became a gel. The molding continued for an elapsed total time of 5 minutes. The polymerized mass was then demolded and its physical properties were measured. The physical properties are listed in Table VI.

TABLE VI

Physical Properties of Copolymer Composed of Caprolactam and the Caprolactam Adduct of the MDI-terminated Polymeg 1000-Based Urethane Prepolymer

| Physical Characteristic | |
|---|---|
| Shore D Hardness | 77 |
| | 5220 psi |

TABLE VI-continued

Physical Properties of Copolymer Composed of Caprolactam and the Caprolactam Adduct of the MDI-terminated Polymeg 1000-Based Urethane Prepolymer

| Physical Characteristic | |
|---|---|
| Tensile Strength, | 36.0 MPa |
| % Elongation | 372 |
| % Tear Strength, pli | 1440 (252 KN/m) |
| Notched Izod Impact ft-lb/in | 7.5 (400 J/M) |
| % Water Absorption at 23° C. | |
| % After 24 hours | 4.28 |
| % After 168 hours | 8.69 |
| Decomposition Temperature °C. by TGA | |
| 2% decomposition | 225 |
| 10% decomposition | 310 |
| 50% decomposition | 370 |

Example 8

A caprolactam adduct of a MDI-terminated-Polymeg 2000-based urethane prepolymer prepared according to Example 7, was copolymerized with caprolactam in the presence of a bromomagnesium lactamate catalyst.

The preparation of isocyanate-terminated prepoloymers using MDI and Polymeg 2000 was as follows.

250 grams of Polymeg 2000 was demoisturized under vacuum. The demoisturized Polymeg 2000 was admixed with 108 grams of MDI (Isonate 143L) in the presence of 0.1% of T-9 (a tin catalyst) at 80° C. It took 75 min. to reach to the theoretical NCO content. The product was very viscous at 80° C., and was very difficult to stir.

Next, a prepolymer was prepared without the use of a tin catalyst at a MDI/Polymeg 2000 molar ratio of 2:1 in the presence of 10 grams of a dioxane solvent.

The reaction was completed in 135 min. at 80° C.

A stoichiometric amount of caprolactam was added to the prepolymer and stirred at 80° C. for 2 hours to obtain a caprolactam adduct. The reaction product was then heated at atmosphereic pressure at 110° C. to remove the dioxane solvent, followed by vacuum distillation to remove the last traces of the dioxane solvent.

The copolymerization of the Polymeg 2000 adduct with caprolactam was conducted in the same manner employed in the previous examples.

The rate of copolymerization of the above adduct with caprolactam is shown in Table VII.

Physical properties of the copolymer are shown in Table VIII.

TABLE VII

Copolymerization of Caprolactam Adduct of MDI-terminated Polymeg 2000-based Urethane Prepolymer at 145° C.

| Product No. | Activator eq. % | Polyether (wt. %) | Catalyst (eq. %) | Cloud Point min. | Solidification min. |
|---|---|---|---|---|---|
| 10 | 1.8 | 12.7 | 4.1 | 19 | 28 |
| 11 | 4.5 | 25.3 | 5.2 | 14 | 22 |
| 12 | 9.1 | 38.3 | 7.0 | 4 | 12 |

TABLE VIII

Properties of Polymeg 2000-based Nylon 6 Copolymer

| Product No. | Tensil Strength psi | 100% Modulus psi | Elongation % | Tear Strength pli | Shore D |
|---|---|---|---|---|---|
| 10 | 2103 | 1506 | 342 | 345 | 48 |
| 11 | 4394 | 1540 | 490 | 637 | 57 |

TABLE VIII-continued

Properties of Polymeg 2000-based Nylon & Copolymer

| Product No. | Tensil Strength psi | 100% Modulus psi | Elongation % | Tear Strength pli | Shore D |
|---|---|---|---|---|---|
| 12 | 1420 | 472 | 354 | 185 | 38 |

Example 9

A mixture was prepared at 80° C. in a reaction kettle. 250 g of water-free Polymeg 2000 was admixed with 42 grams of hexamethylene diisocyanate (HDI) in the presence of 10 grams of dioxane. The Polymeg 2000 and HDI reacted to form a prepolymer. A stoichiometric amount of caprolactam was added at 80° C. while stirring fro 2 hours in order to obtain a caprolactam adduct. After evaporation of the dioxane, 55.6 grams of the adduct and 40 grams caprolactam were heated at 95° C. (solution A). Separately a solution of 19.5 g lactam magnesiumbromide (1 molar in caprolactam) in 60 g caprolactam was made at 95° C. (solution B). Solution A and Solution B were mixed together and the mixture of solution A and solution B poured into a mold at 160° C. After 15 minutes at 160° C. the nylon molded copolymer was demolded. The nylon copolymer had 25 wt % polyether. The molded object composed of nylon copolymer showed a flexural modulus of 1129 MPa and a notched Izod Impact strength of 261 J/M.

Example 10

Absolutely dry ξ-caprolactam was used throughout these experiments. A two component system was prepared by using two test tubes, i.e. potassium caprolactam and ξ-caprolactam in an amount shown in the tables (IX-XII) were charged in a test tube. The polyether-based adduct and ξcaprolactam in an amount shown in the tables were charged in another test tube. Bath test tubes were dipped in an oil bath kept at 95° C.

When the two components reached 95° C. the one component was charged into the other test tube and shaked vigorously for 5 seconds, and then test tube was immediately immersed into an oil bath kept at 130° C. and dry nitrogen bulle was put on the surface of the reaction mixture for blanket. A glass rod was used for agitation and gel and solidification times were measured.

The results obtained are shown in Tables IX through XII.

In the tables various abbreviations are used. CLM stands for caprolactam. KL stands for potassium lactamate. HDI stands for 1,6 hexamethylene diisocyanate. Nyrim catalyst means bromomagnesium caprolactam.

TABLE IX

| | Product No. | | | | | |
|---|---|---|---|---|---|---|
| | 13 | 14 | 15 | 16 | 17 | 18 |
| Polyol, wt. % | 10.2 | 10.2 | 10.2 | 20.2 | 20.2 | 30.3 |
| CLM, g | 30.6 | 29.2 | 25.0 | 23.6 | 20.1 | 15.0 |
| KL (2 eq/kg), g | 3.0 | 4.4 | 8.6 | 3.7 | 7.2 | 5.9 |
| Polymeg 1000/DHI/CLM (2/1) Adduct, g | 6.4 | 6.4 | 6.4 | 12.7 | 12.7 | 19.1 |
| Total CLM, g | 34.3 | 34.2 | 33.9 | 28.9 | 28.6 | 23.2 |
| Free CLM, g | 32.7 | 32.3 | 31.0 | 25.1 | 25.1 | 19.1 |
| Free CLM + CLM in adduct, g | 33.6 | 33.2 | 31.9 | 26.0 | 26.0 | 20.0 |
| Total Wt., g | 40 | 40 | 40 | 40 | 40 | 40 |
| Total CLM, wt. % | 85.8 | 85.5 | 84.8 | 72.2 | 71.5 | 58.8 |
| meq., Free CLM | 289 | 286 | 274 | 222 | 222 | 169 |
| meq., KL | 6.0 | 8.8 | 17.2 | 7.4 | 14.4 | 11.8 |
| meq., Adduct | 8.3 | 8.3 | 8.3 | 16.5 | 16.5 | 24.8 |
| eq. ratio, K./CLM, % | 2.1 | 3.1 | 6.3 | 3.3 | 6.5 | 7.0 |
| eq. ratio, Adduct/CLM, % | 2.9 | 2.9 | 3.0 | 7.4 | 7.4 | 14.7 |
| eq. ratio, KL/Adduct | 0.7 | 1.1 | 2.1 | 0.4 | 0.9 | 0.5 |
| CLM/Adduct, kg/eq. | 3.9 | 3.9 | 3.7 | 1.5 | 1.5 | 0.8 |
| A Stream, °C.* | 95 | 95 | 95 | 95 | 95 | 95 |
| B Stream °C.* | 95 | 95 | 95 | 95 | 95 | 95 |
| Mixing temp., °C. | 95 | 95 | 95 | 95 | 95 | 95 |
| Polymerization temp., °C. | 130 | 130 | 130 | 130 | 130 | 130 |
| Gel time, min. | 2'15" | 1'40" | 1'45" | 2'20" | 55" | 1'25" |
| Solidification time, min. | 2'30" | 1'55" | 2'20" | 2'40" | 1'55" | 5'25" |

*A Component: KL + CLM
**B Component: Adduct + CLM

TABLE X

| | Product No. | | |
|---|---|---|---|
| | 19 | 20 | 21 |
| Polyol, wt. % | 20.1 | 20.1 | 20.1 |
| CLM, g | 24.4 | 23.2 | 19.8 |
| KL (2 eq/kg), g | 2.5 | 3.7 | 7.1 |
| Polymeg/H₆XDI/CLM (2/1) Adduct, g | 13.1 | 13.1 | 13.1 |
| Total wt., g | 40 | 40 | 40 |
| Total CLM, g | 28.6 | 28.5 | 28.2 |
| Free CLM, g | 26.1 | 25.8 | 24.8 |
| Free CLM + CLM in adduct, g | 28.0 | 27.7 | 26.7 |
| meq., Free CLM | 231 | 228 | 219 |
| meq., KL | 5.0 | 7.4 | 14.2 |
| meq., Adduct | 16.5 | 16.5 | 16.5 |
| eq. ratio, KL/CLM, % | 2.2 | 3.2 | 6.5 |
| eq. ratio, Adduct/CLM, % | 7.1 | 7.2 | 7.5 |
| eq. ratio K./Adduct | 0.31 | 0.44 | 0.87 |
| CLM/Adduct, kg/eq. | 1.7 | 1.7 | 1.6 |
| A Component, °C.* | 95.0 | 95.0 | 95.0 |
| B Component, °C.* | 95.0 | 95.0 | 95.0 |
| Mixing temp., °C. | 95.0 | 95.0 | 95.0 |
| Polymerization temp., °C. | 130 | 130 | 130 |
| Gel time, $T_g$ | 2'30" | 1'20" | 55" |
| Solidification time, $T_S$ | 2'50" | 1'55" | 1'30" |

*A Component: KL + CLM
B Component: Adduct + CLM

TABLE XI

| | Product No. | | | |
|---|---|---|---|---|
| | 22 | 23 | 24 | 25 |
| Polyol, wt. % | 20 | 20 | 20 | 20 |
| CLM, g | 24.2 | 23.1 | 21.9 | 18.7 |
| KL (2 eq/kg), g | 1.2 | 2.3 | 3.5 | 6.7 |
| *Polymeg 1000 100/Isonate 143L/CLM (2/1) Adduct, g | 14.6 | 14.6 | 14.6 | 14.6 |
| Total wt., g | 40 | 40 | 40 | 40 |
| Total CLM, g | 27.2 | 27.1 | 27.0 | 26.7 |

TABLE XI-continued

| | Product No. | | | |
|---|---|---|---|---|
| | 22 | 23 | 24 | 25 |
| Free CLM, g | 25.0 | 24.7 | 24.3 | 23.4 |
| Free CLM + CLM in adduct, g | 26.9 | 26.6 | 26.2 | 25.3 |
| meq., Free CLM | 221 | 219 | 215 | 207 |
| meq., KL | 2.4 | 4.6 | 7.0 | 13.4 |
| meq., Adduct | 16.4 | 16.4 | 16.4 | 16.4 |
| eq. ratio, KL/CLM, % | 1.1 | 2.1 | 3.3 | 6.5 |
| eq. ratio, Adduct/CLM, % | 7.4 | 7.5 | 7.6 | 8.0 |
| eq. ratio, KL/Adduct | 0.15 | 0.28 | 0.43 | 0.81 |
| CLM/Adduct, kg/3 q. | 1.6 | 1.6 | 1.6 | 1.5 |
| A Stream, °C.** | 95 | 95 | 95 | 95 |
| B Stream, C.** | 95 | 95 | 95 | 95 |
| Mixing temp., °C. | 95 | 95 | 95 | 95 |
| Polymerization temp., °C. | 130 | 130 | 130 | 130 |
| Gel time, $T_g$ | <30′ | <30′ | 19′10″ | 3′55″ |
| Solidification time, $T_S$ | | | 28′00″ | 8′05″ |

*Polymeg 1000/Isonate 143L/CLM Adduct (2/1) prepared without dioxane solvent.
**A Component: KL + CLM
B Component: Adduct + CLM

TABLE XII

| | Product No. | |
|---|---|---|
| | 26 | 27 |
| Polyol, wt. % | 25 | 30 |
| CLM, g | 100 | 100 |
| Caprolactam magnesium bromide* | 19.45 | 19.45 |
| Polymeg 2000/HDI/CLM adduct (2/1), g | 55.6 | 73.1 |
| Total CLM, g | 122 | 124 |
| Free CLM, g | 115 | 115 |
| Free CLM + CLM in adduct, g | 120 | 122 |
| Wt. % total CLM | 69.8 | 64.4 |
| meq. Free CLM | 1020 | 1020 |
| meq. Nyrim catalyst | 19.4 | 19.4 |
| meq. adduct | 42.1 | 55.3 |
| eq. ratio, Cat./CLM, % | 1.9 | 1.9 |
| eq. ratio, Adduct/CLM, % | 4.1 | 5.4 |
| eq. ratio, Cat./adduct | 0.46 | 0.35 |
| CLM/Adduct, kg/eq. | 2.9 | 2.2 |
| Temperature, A Stream, °C.** | 100 | 100 |
| B Stream, °C.** | 100 | 100 |
| Mixing Temp., °C. | 100 | 100 |
| Molding Temp., °C. | 160 | 160 |
| Molding time, min. | 15 | 20 |
| Gel time, $t_g$ | 12′00″ | 14′30″ |
| Solidification time, $t_s$ | 12′30 | 15′45″ |
| Flexural modulus, MPa | 896 | 306 |
| Izod impact, J/m | 258 | 815(IB)*** |
| Shore D | 68 | 61 |

*One equivalent/kg.
**A Component: caprolactam magnesium bromide + CLM.
B Component: Adduct + CLM.
***IB: Incompletely broken.

What is claimed:

1. An N-substituted carbamoyl-lactam compound of the formula:

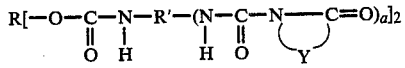

wherein R is a di-valent hydrocarbon radical derived from polytetramethyleneglycol and represents the radical remaining from the polytetramethylene oxide starting material used in preparing polytetramethylene-glycol, said polytetramethylene glycol having a hydroxyl equivalent weight of 300 to 3000, wherein R' is a di-valent hydrocarbon radical derived from a diisocyanate selected from the group consisting of 1,5 hexane diisocyanate, 1,6 hexane diisocyanate, isophorone diisocyanate, xylylene diisocyanate, 2,2'-diphenylmethane diisocyanate, 2,4'-diphenylmethane diisocyanate, 4,4'-diphenylmethane diisocyanate, hydrogenated 2,2'-diphenylmethane diisocyanate, hydrogenated 2,4'-diphenylmethane diisocyanate, hydrogenated 4,4'-diphenylmethane diisocyanate, hydrogenated xylylene diisocyanate, hydrogenated 2,4-toluene diisocyanate, hydrogenated 2,6-toluene diisocyanate and mixtures thereof, Y is a $C_3$–$C_{14}$ alkylene group, and a is a value corresponding to the mean functionality of said polyisocyanate minus 1.

2. A compound according to claim 1 wherein the equivalent weight of said polytetramethylene ether glycol is about 1000 to about 2500.

3. An N-substituted carbamoyl-lactam compound of the formula:

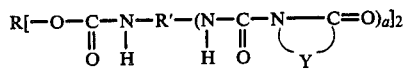

wherein R is a di-valent hydrocarbon radical derived from polytetramethyleneglycol and represents the radical remaining from the polytetramethylene oxide starting material used in preparing polytetramethylene-glycol, said polytetramethylene glycol having a hydroxyl equivalent weight of 1000 to 2500, wherein R' is a di-valent hydrocarbon radical derived from a diisocyanate selected from the group consisting of 1,5 hexane diisocyanate, 1,6 hexane diisocyanate, isophorone diisocyanate, xylylene diisocyanate, 2,2'-diphenylmethane diisocyanate, 2,4'-diphenylmethane diisocyanate, 4,4'-diphenylmethane diisocyanate, hydrogenated 2,2'-diphenylmethane diisocyanate, hydrogenated 2,4'-diphenylmethane diisocyanate, hydrogenated 4,4'-diphenylmethane diisocyanate, hydrogenated xylylene diisocyanate, hydrogenated 2,4-toluene diisocyanate, hydrogenated 2,6-toluene diisocyanate and mixtures thereof, Y is alkylene group having from 4 to 10 carbon atoms, and a is a value corresponding to the mean functionality of said polyisocyanate minus 1.

4. The N-substituted carbamoyl-lactam compound of claim 1, wherein Y is the alkylene group residue of a lactam selected from the group consisting of 2-pyrrolidone, 2-piperidone, lauryl lactam, caprolactam, 6-amino-5-methyl hexanoic acid lactam, 6-amino-3-methyl hexanoic acid lactam, and mixtures thereof.

5. An N-substituted carbamoyl-lactam compound of the formula

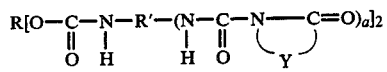

wherein R is a di-valent hydrocarbon radical derived from polytetramethylene glycol and represents the radical remaining from the polytetramethylene oxide starting material used in preparing polytetramethylene-glycol, said polytetramethylene glycol having a hydroxyl equivalent weight of 300 to 3000, wherein R' is a multi-valent hydrocarbon radical residue derived from a polyisocyanate having an isocyanate functionality greater than 2, Y is a $C_{3-14}$ alkylene group, a has a value corresponding to the mean functionality of said polyisocyanate-1.

6. The N-substituted carbamoyl-lactam compound of claim 5, wherein y is the alkylene group residue of a lactam selected from the group consisting of 2-pyrrolidone, 2-piperidone, laurl lactam, caprolactam, 6-amino-5-methyl hexanoic acid lactam, 6-amino-4-methyl hexanoic acid lactam, and mixtures thereof.

7. A process for preparing a lactam compound which consists essentially in mixing and adding a hydroxyl compound having the formula:

$R(OH)_2$ wherein $R(OH)_2$ is a polyetramethylene glycol, R is the hydrocarbon radical remaining from the polytetramethylene glycol, said glycol compound having an equivalent weight of 300 to 3000, with a polyisocyanate having the formula:

$R'(NCO)_{a+1}$ wherein R' is a radical derived from a polyisocyanate selected from the group consisting of 1,5 hexane diisocyanate, 1,6 hexane diisocyanate, isophorone diisocyanate, xylylene diisocyanate, 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, polyphenylene polymethylene polyisocyanate, hydrogenated 2,2'-diphenylmethane diisocyanate, hydrogenated 2,4'-diphenylmethane diisocyanate, hydrogenated 4,4'-diphenylmethane diisocyanate, hydrogenated xylylene diisocyanate, hydrogenated 2,4-toluene diisocyanate, and hydrogenated 2,6-toluene diisocyanate and mixtures thereof;

and reacting the intermediate product thus formed with at least one lactam whereby there is obtained a lactam compound having the formula:

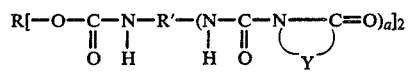

wherein R and R' have the aforestated meanings, Y is a 3 to 14 carbon alkylene group, and a is the functionality of said polyisocyanate minus 1.

8. A process according to claim 7 vherein the equivalent weight of said polytetramethylene ether glycol is about 1000 to about 2500.

9. The process according to claim 7 wherein said lactam is selected from the group consisting of 2-pyrrolidone, 2-piperidone, lauryl lactam, caprolactam, 6-amino-5-methyl hexanoic acid lactam, 6-amino-3-methyl hexanoic acid lactam, and mixtures thereof.

* * * * *

UNITED STATES PATENT AND TRADEMARK OFFICE
CERTIFICATE OF CORRECTION

PATENT NO. : 4,626,385

DATED : December 2, 1986

INVENTOR(S) : Kaneyoshi ASHIDA

It is certified that error appears in the above-identified patent and that said Letters Patent is hereby corrected as shown below:

Col. 15, line 8, "wherein y is" should be --wherein Y is--;

line 10, "laurl lactam" should be --lauryl lactam--; and line 22, "claim 7 vherein" should be --claim 7 wherein--.

Signed and Sealed this

Seventeenth Day of March, 1992

Attest:

HARRY F. MANBECK, JR.

*Attesting Officer* — *Commissioner of Patents and Trademarks*